United States Patent

Kushibe et al.

[11] Patent Number: 5,912,385
[45] Date of Patent: Jun. 15, 1999

[54] PROCESS FOR THE PRODUCTION OF PURE ALKANESULFONIC ACIDS

[75] Inventors: Kazuyoshi Kushibe, Fujinomiya; Hiromitsu Kobayashi, Fuji; Hirohisa Nitoh, Fuji; Hirotsugu Kitamura, Fuji, all of Japan

[73] Assignee: Tokai Denka Kogyo Kabushiki Kaisha, Tokyo, Japan

[21] Appl. No.: 09/009,449

[22] Filed: Jan. 20, 1998

[30] Foreign Application Priority Data

Jan. 20, 1997 [JP] Japan ................................. 9-007177

[51] Int. Cl.$^6$ .................................................. C07C 303/00
[52] U.S. Cl. ............................................ 562/118; 562/108
[58] Field of Search ...................................... 562/108, 118

[56] References Cited

U.S. PATENT DOCUMENTS 4,987,250  1/1991  McGee et al. .......................... 562/118

*Primary Examiner*—Brian M. Burn
*Assistant Examiner*—Brian J. Davis
*Attorney, Agent, or Firm*—Scully, Scott, Murphy & Presser

[57] ABSTRACT

This invention relates to a process for the production of an alkanesulfionic acid such as isethionic acid with a high purity in a high yield and at a low cost by oxidation of a (hydroxy)alkylmercaptan with hydrogen peroxide characterized in that a whole amount beyond a stoichiometric amount of a solution of hydrogen peroxide having a $H_2O_2$ concentration of not less than 50% by weight is charged into a reaction vessel, said mercaptan is continuously fed at a temperature of 50° C. or lower, aging is carried out, distillation with boiling is carried out and then the reaction mixture is contacted with an anion exchanger.

6 Claims, No Drawings

PROCESS FOR THE PRODUCTION OF PURE ALKANESULFONIC ACIDS

FIELD OF THE INVENTION

This invention relates to a process for the production of an alkylsulfonic acid by the reaction of hydrogen peroxide with an alkylmercaptan, and, more particularly, it is concerned with a process for the production of an alkanesulfonic acid with a high purity in a far higher yield and at a lower cost.

BACKGROUND OF THE INVENTION

An alkanesulfonic acid having the general formula

$$R-(CH_2)xCH_2-SO_3H$$

wherein R is a hydrogen atom or the group —OH and x is an integer of $0 \leq x \leq 8$ is publicly known and has been applied for various uses. In particular, a hydroxyalkanesulfonic acid which is encompassed within the above general formula, inter alia, 2-hydroxyethanesulfonic acid also referred to as isethionic acid has a wide variety of its utilities. For example, its ester with acrylic acid or methacrylic acid has been used as a reactive emulsifying agent, while its homopolymers or copolymers with vinyl monomers have been employed as a flocculating agent, a dispersing agent, a thickening agent and a flame retardant and the like. Also, its ester with a long chain alkylcarboxylic acid can have an excellent activity as a surfactant and has been widely employed in the field of detergents or cosmetics. Moreover, it has recently been expected typically as bonding agents for basic dyestuffs, adhesives, additives for tin- or tin solder-plating electrolytic bath and its usage has been widely spread.

There have been hitherto proposed a variety of processes for the preparation of an alkanesulfonic acid typically 2-hydroxyethanesulfonic acid(isethionic acid).

There has been proposed, for example, by Baumstark, et al. in Chern. Ber.,1867, p. 586 a process wherein ethylene is treated with a sulfonating agent such as chlorosulfonic acid or the like or a process wherein ethylene oxide is treated with gaseous sulfurous acid.

However, it is found that the alkanesulfonic acids produced by these processes are contaminated with unfavorable impurities such as organic chlorinated products, sulfuric acid, organic sulfates or the like and are the products not suited for various application fields such as surfactants, additives for polymers and the like.

In view of this, many studies have been made for the production of an alkanesulfonic acid having a less content of impurities.

For example, Koening et al. in U.S. Pat. No. 2,892,852 have proposed a process wherein an organic thioether or a thioacetic acid ester is reacted with peracetic acid in an acetic acid solution to produce the corresponding sulfonic acid, while there has been proposed a process wherein ozone or a permanganate salt is used as an oxidizing agent in Journal Praktiche Chemie, (4), (2), Vol. 27, (1955), pp. 241–242. However, such processes have the problems of oxidizing agents being expensive or an obtainable yield being low so that they have not substantially been utilized in an industrial scale.

And, U.S. Pat. No. 4,499,028 to Longley et al. or Japanese Patent Kokai Application No. 32049/1990 by Itoh et al. disclosed a process wherein an alkali salt of isethionic acid with a high yield, which is obtained by reacting ethylene oxide with an alkali salt of bisulfuric acid according to a well-known procedure, is contacted with anhydrous hydrogen chloride in a water-miscible solvent such as an alcohol or the like. However, this process has the drawbacks that a corrosive gas is to be used and also a troublesome procedure for removing by-products of inorganic salts is to be adopted so that it is not advantageous for industrial application.

Further, U.S. Pat. No. 2,727,920 disclosed a process wherein methylmercaptan is subjected to electrolytic oxidation or oxidation with nitric acid. However, a low yield is provided in the former case, while acceleratedly raising reaction temperature should be controlled in the latter case and both are unsuited for industrial application.

On the other hand, hydrogen peroxide has favorable conditions such as inexpensive availability, safe handling and by-production of only water after completion of the reaction and the like as compared with other oxidizing agents, and then there have been made various studies to utilize it for the sulfonation reaction of mercaptan, besides the aforementioned processes.

For example, Showell et al. proposed in Journal of Organic Chemistry, Vol. 27, (1962), pp. 2853–2858 a process for the production of sulfonic acid by the oxidation of mercaptan using hydrogen peroxide in a system containing a sufficient amount of an organic acid to produce an organic peracid. However, the product obtained according to this process is contaminated with the residual carboxylic acid and percarboxylic acid Moreover, an alkanesulfonic acid, particularly isethionic acid is difficult to be purified by means of those separation techniques widely used for removal of such impurities such as a solvent extraction method, a distillation method or the like owing to its intrinsic properties of solubility in various solvents, boiling point, polarity and the like. Then, it is highly disadvantageous in an industrial scale to carry out the oxidation with a peracid in situ as described above.

Deschrijver et al. proposed a process for the production of an alkanesulfonic acid by oxidation of an alkylmercaptan with hydrogen peroxide using as a catalyst a molybdenum or tungsten derivative. However, this process presented the problem of the product being colored and further resulted in prevention of the product from utilization in other application field, owing to the coexisting catalyst.

McGee et al. proposed in U.S. Pat. Nos. 4,910,330 and 4,987,250 a process for the production of an alkanesulfonic acid by oxidation of an alkylmercaptan with hydrogen peroxide without the aforementioned problems such as contamination of an organic acid or a catalyst.

The process by McGee et al. is excellent in that an alkanesulfonic acid can be produced without any contamination of the product by undesirable additives, but there may be required troublesome steps wherein conc. hydrogen peroxide is diluted with water (for example, up to about 30% by weight)and subsequently the dilution water (and the water by-produced during the reaction) is distilled off to conduct a temperature control in order to remove violent reaction heats. Further, in contacting raw materials with an oxidizing agent, an alkylmercaptan and hydrogen peroxide should be simultaneously fed to a portion of the hydrogen peroxide required for the reaction with exact analysis to effect flow control so as to be always an excess of $H_2O_2$ in an excess amount in the extremely limited range more approximate to a stoichiometric amount to the raw material, an alkylmercaptan, and then the reaction steps become complicated, which leads to the drawback that both yield and purity of the so-obtained product may be variable.

Moreover, oxidation is carried out at a reaction temperature substantially beyond 60° C. to afford many undesired by-products of impurities such as sulfuric acid or an organic acid. Furthermore, although a theoretically slightly excess amount of hydrogen peroxide is used to an alkylmercaptan, an amount of the hydrogen peroxide to be used is actually insufficient to complete oxidation of an alkylmercaptan under the aforementioned conditions, whereby, as a matter of fact, the reaction intermediates such as disulfides or the like may remain and the product may be contaminated.

Accordingly, the product prepared by this process is insufficient in a product purity to be applied for the general use of an alkanesulfonic acid, particularly, hydroxyethanesulfonic acid.

As explained above, the processes as described in U.S. Pat. Nos. 4,910,330 and 4,987,250 involves the serious problems as depicted above for the production using a scale-up or large equipment and thus they are not perfectly satisfactory in an industrial aspect.

SUMMARY OF THE INVENTION

We have made our earnest studies to solve the problems with the prior art processes in reference to a process which comprises reacting an alkylmercaptan with hydrogen peroxide, and as a result found out a process wherein an alkanesulfonic acid of a high utilization value can be produced with a high purity and a high yield without any need for complicate procedures by eliminating the production of impurities which may contaminate the product, and this invention has been completed upon this finding.

More specifically, this invention relates to a process for the production of an alkanesulfonic acid having the general formula (I)

$$R-(CH_2)_xCH_2-SO_3H \qquad (I)$$

(wherein R is a hydrogen atom or a group of —OH and x is an integer of $0 \leq x \leq 8$) by oxidizing using hydrogen peroxide the mercapto group of an alkylmercaptan having the general formula (II)

$$R-(CH_2)_xCH_2-SH \qquad (II)$$

(wherein R and x are as defined above) characterized in that an aqueous hydrogen peroxide solution in the whole amount is charged into a reaction vessel, said aqueous hydrogen peroxide solution having a $H_2O_2$ concentration of not less than 50% by weight and having a $H_2O_2$ amount of not less than 3.10 moles per mole of said alkylmercaptan, said alkylmercaptan is substantially continuously fed to said reaction vessel at a reaction temperature always not beyond 50° C. and thereafter an aging period is provided and the reaction mixture is subsequently subjected to distillation with boiling and then said reaction mixture is contacted with an anion exchanger to produce a pure alkanesulfonic acid.

According to the process of this invention, there can be produced the desired alkanesulfonic acid at a low cost, in a high yield and with a high purity.

DETAILED DESCRIPTION OF THE INVENTION

The hydrogen peroxide which may be used in this invention may be any of commercially available products and its concentration should be not less than 50% by weight, and an aqueous solution thereof usually of not more than 90% by weight, preferably 55~65% by weight may be used, whereby an energy cost can be minimized for a concentration step to increase a concentration of the final product of an alkanesulfonic acid up to an extremely high level and a far higher yield of the product can be accomplished.

Specific examples of the alkylmercaptan represented by the general formula (II) may include single compounds such as methylmercaptan, ethylmercaptan, propylmercaptan, butylmercaptan, hydroxymethylmercaptan, 2-mercaptoethanol, 3-mercaptopropanol, 4-mercaptobutanol and the like and a mixture thereof. The oxidized product obtained by using said alkylmercaptan may be represented by the general formula (I) , including the corresponding methanesulfonic acid, elhanesulfonic acid, propanesulfonic acid, butanesulfonic acid, hydroxymethanesulfonic acid, 2-hydroxyethanesulfonic acid(isethionic acid), 3 -hydroxypropanesulfonic acid, 4-hydroxybutanesulfonic acid and the like.

The process of this invention can provide the most superior results particularly when said alkylmercaptan is 2-mercaptoethanol and its oxidized product is 2-hydroxyethylsulfonic acid(isethionic acid) and then this non-limiting embodiment will be explained in detail hereafter. The reaction of 2-mercaptoethanol with hydrogen peroxide may be carried out under atmospheric pressure at a temperature ranging not higher than 50° C., usually 10~50° C., and the reaction is desirably carried out at 30~50° C., in particular, 40~45 C., whereby the production of impurities by-producted by the oxidative decomposition with $H_2O_2$ such as sulfuric acid, a lower aliphatic acid or the like may be prevented.

In reacting 2-mercaptoethanol with hydrogen peroxide, 2-mercaptoethanol and hydrogen peroxide are required usually in a stoichiometric amount on a genuine basis, that is, at 3 moles of hydrogen peroxide per mole of 2-mercaptoethanol, but it is significant to use an excess amount of hydrogen peroxide in order to prevent undesired reaction intermediates from remaining. In this invention, hydrogen peroxide can be used in the range of usually not less than 3.10 moles up to not more than 40 moles, preferably 3.10~3.5 moles, per i mole of 2-mercaptoethianol. It is more desirable from the standpoint of a production cost to use hydrogen peroxide in the range of 3.15~3.20 moles.

According to the preferred embodiment of this invention, the whole of hydrogen peroxide can be previously charged into the reaction solution and then 2-mercaptoethianol can be fed in a constant amount thereinto with a proper stirring. The flow rate in the feeding at that time may be in the range sufficient to maintain a prescribed reaction temperature in compliance with cooling capacity of the reaction vessel, and it is preferable to add the 2-mercaptoethanol illustratively over 3~10 hours, desirably 4~8 hours, particularly about 6 hours, more or less, whereby complicated procedures may be avoided and a steady temperature control may be effected.

In the process of this invention, it is essential to provide an aging period after completion of the addition of 2-mercaptoethanol. The aging period may be usually 3~20 hours, desirably 6~10 hours, particularly preferably about 8 hours, more or less, whereby the production of undesired impurities capable of contaminating the product can be prevented. Aging temperature may be desirably in the range that could not induce any side reactions or any excessive oxidation of the isethionic acid as produced, in particular, a temperature of 20~50° C. which is within the temperature range in feeding 2-mercaptoethanol, in view of easiness of procedures and cost.

At this stage, 90~95% of the initial charge amount of hydrogen peroxide is consumed, while there can be confirmed the production of isethionic acid at 90~95%, sulfuric acid at 2~6%, low molecular compounds such as acetic acid or acetaldehyde at 1~5% and intermediates not yet converted to isethionic acid(for example, partial oxidized products of disulfide derivatives) at 3~8%.

The reaction mixture after completion of the aging is then subjected to distillation treatment with boiling. This distillation can be carried out by heating at a temperature to maintain the boiling of the reaction mixture under atmospheric pressure, for example, a temperature in the range from 100° C. to 120° C., usually for 1~7 hours, preferably 2~4 hours, whereby there can be obtained isethionic acid with a high purity by converting undesired residual reaction intermediates to the desired product.

It is desirable to distill off a whole amount of the steam under reflux or a part thereof by blowing air, steam or an inert gas such as nitrogen or the like into the reaction system (flushing) during the above heat treatment. This procedure is effective for obtaining a higher concentration of isethionic acid and further significant,in particular, for complete removal of a low boiling lower aliphatic acid, a lower alcohol and an aldehyde which may remain in the reaction liquid having the above composition.

This distillation treatment can offer the advantage that the residual reaction intermediates can be completely converted to isethionic acid, in addition to the removal of lower aliphatic acids to afford a far more improved yield.

According to the process of this invention, it is essential that an aqueous solution containing a high concentration of isethiionic acid obtained after completion of the oxidation reaction is contacted with an anion exchanger, especially a weakly basic ion exchanger.

The aqueous solution obtained according to the oxidation reaction of this invention which has usually an isethionic acid concentration of 40~60% by weight and a sulfuric acid concentration of 1.8~2.5% by weight can be contacted with a weakly basic ion exchanger to perform a selective adsorption of only those acid contents which could not be removed by flushing distillation, such as sulfuric acid, sulfoacetic acid an the like, thereby accomplishing the purification thereof.

The weakly basic ion exchangers which may be preferably employed in the process of this invention are those weakly basic ion exchangers having as an ion-exchange group a tertiary amine or polyamine. The tertiary amine as used herein is meant to indicate, for example, a compound represented by the following general formula (III)

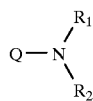

(III)

wherein Q is an acrylic, styrene or phenol polymer group and R1 and R2 may be the same or different and each represents an alkyl group. As the polyamine, there may be preferably employed any straight or branched amine having the above general formula (III) wherein $R_1$ is a hydrogen atom and $R_2$ is an ethylenediamine as a unit. Any shape of the weakly basic ion exchanger may be utilized if commercially available and those resins with a shape of short fibers, a ground product or beads may be recommended in view of their general-purpose properties.

The ion exchangers which may be suitably employed in this invention may specifically include the following ones shown in terms of their trade names:

Duolite A-561, A-568, A-375, A-368, A-378 and A-7;
Diaion WA10, WA11, WA20, WA21 and WA30;
Amberlite IRA-35, IRA-60E, IRA-68, IRA-93ZU and IRA-945; and others.

A passing velocity of a treating liquid SV may be in the range of 0.1~2 which is generally applied, and SV is preferably in the range of 0.2~1.0, particularly 0.4~0.6, in order to recover the desired isethionic acid at a higher purity.

A method for contacting with a weakly basic ion exchanger is not particularly critical and there may be used any conventional method, for example, a method wherein the reaction mixture containing isethionic acid is passed downflow or upflow through said resin previously packed into a resin column.

An operation temperature is not particularly critical and the desired product having sufficiently high yield and purity can be obtained at ordinary temperature.

The product at this stage may be usually applied to every well-known uses, but, if coloration of the isethionic acid solution is observed with deterioration of the resin, the reaction mixture after the above treatment may be then passed through an organic material-absorbing resin for example, Amberlite XAD-4 to perform decolorization.

According to this invention, isethionic acid may be always obtained in a high yield of 95~97% and with a high purity of 99% or more.

The isethionic acid thus produced is inexpensive with a high concentration and a high purity in view of easy and definite production thereof, and may be effectively utilized for various uses in the field of polymer industry and organic chemical industry.

As depicted above, the process of this invention can be similarly applied to the production of the alkanesulfonic acid of the above general formula (I) from the alkylmercaptan of the above general formula (II).

DESCRIPTION OF THE PREFERRED EMBODIMENTS

This invention will be more fully explained by way of the following examples, but this invention is not limited to these examples.

EXAMPLE 1

To a glass reaction vessel equipped with an internal condenser, a stirrer, a condenser with an opening and shutting cock for removal of a solvent and a liquid inlet tube was added 357 g(6.3 mol) of 60% by weight hydrogen peroxide all at once and then 156 g(2.0 mol) of 2-inercaptoethanol was continuously fed from the liquid inlet tube at 0.4 ml/min. while the reaction mixture was vigorously stirred. During the period of this feeding, a liquid temperature was kept at 45° C. by adjusting a volume of the cooling water supplied to the condenser.

After completion of 2-mercaptoethanol, stirring was continued at room temperature for 10 hours. At this stage, there was afforded a 43.2% by weight isethionic acid solution in water(Yield 221.8 g:88%). Also, in addition to 1.1% by weight sulfuric acid(Yield 5.6 g), 2.5% by weight hydrogen peroxide(Yield 12.8 g), there were contaminated low boiling compounds such as 2-hydroxyethyl disulfide polyoxide, acetaldehyde, acetic acid and the like.

The reaction mixture was heated to 110° C. under atmospheric pressure with vigorous stirring. At this point, a nitrogen gas was blown through via a sample inlet tube to remove off a part of steam out of the reaction system.

After 5 hours, there was given a 55.0% by weight aqueous solution of isethionic acid(Yield 241.9 g:96.0%). In this conc. aqueous isethionic acid solution thus obtained, there was not confirmed any other by-products involved therein than sulfuric acid at a productivity of 2.8% and sulfonated acetic acid at a productivity of 0.2%.

The reaction mixture was passed through a 35 mmϕcolumn packed with "Duolite A-561" (manufactured by Sumitomo Chemical Co.,Ltd.) which had been regenerated with an alkaline aqueous solution at SV 0.5 from the column top (downflow).

The concentrations of isethionic acid and sulfuric acid were quantitatively analyzed by means of an ion chromatography and a neutralization titration.

A 54.0% by weight aqueous isethionic acid solution (Yield 241.6 g 95.9%) has a content of sulfuric acid of 0.1% by weight only (Purity of isethionic acid: 99.9%).

EXAMPLE 2

Example 1 was repeated except that an oxidation reaction temperature when 2-mercaptoeLhanol was added was changed to 25° C.

There was obtained a 50.2% by weight aqueous isethionic acid solution (Yield 234.4 g: 93.0%). The residual amount of sulfuric acid was not more than 0.1% by weight (Purity of isethionic acid:99.8%).

COMPARATIVE EXAMPLE 1

The reaction was carried out in the same manner as described in Example 1 except that the aging period after completion of the addition of 2-mercaptoethanol was not provided.

Yield of isethionic acid was 221.8 g (Yield 88.0% ). Contamination of low boiling compounds was not observed, but contamination of mono- or poly-oxides such as 2-hydroxyethyl sulfide or 2-hydroxyetliyl disulfide was confirmed in the solution afforded after treatment of the resin. The solution was slightly yellowish-brown colored.

COMPARATIVE EXAMPLE 2

The reaction was carried out in the same manner as described in Example 1 except that the reaction rate of $H_2O_2$/2-mercaptoethanol was changed to 3.05/1.0(mole/mole).

Yield of isethionic acid was 209.2 g (Yield 83.1% ). Contamination of impurities such as the reaction intermediate, 2-hydroxyetllíyl disulfide, and mono- or poly-oxide thereof and the like was confirmed in the resulting solution. The solution was slightly yellowish-brown colored.

COMPARATIVE EXAMPLE 3

The reaction was carried out in the same manner as described in Example 1 except that a concentration of hydrogen peroxide was changed to 35% by weight, an oxidation reaction temperature was changed to 66° C. and treatment of resin was not applied.

Yield of isethionic acid was 204.1 g (Yield 81.0%). By-production of sulfuric acid was so high as 9.7% in terms of its productivity and in addition, contamination of impurities such as the reaction intermediate, 2-hydroxyethyl disulfide, and oxides thereof, sulfoacetic acid and the like was confirmed. The solution was brown colored.

What is claimed is:

1. A process for the production of an alkanesulfonic acid having the general formula $R-(CH_2)_xCH_2-SO_3H$, wherein R is hydrogen or hydroxyl; and x is 0 or an integer of 1 to 8 comprising the steps of:

(a) introducing an aqueous hydrogen peroxide solution into a reaction vessel, said aqueous hydrogen peroxide solution having a hydrogen peroxide concentration of at least 50% by weight;

(b) continuously feeding an alkylmercaptan having the general formula $R-(CH_2)_xCH-SH$, where R and x have the meanings given above, into said reaction vessel such that said reaction vessel contains at least 3.1 moles of hydrogen peroxide per mole of said alkylmercaptan and wherein said reaction vessel is maintained at a temperature not in excess of 50° C., with the proviso that said alkylmercaptan is not fed into said reaction vessel until all of said aqueous hydrogen peroxide solution is introduced therein, wherein a reaction mixture is formed;

(c) aging said reaction mixture;

(d) boiling and distilling said aged reaction mixture; and (e) contacting said boiled and distilled reaction mixture with an anion exchanger to selectively remove sulfuric acid and sulfoacetic acid.

2. A process as claimed in claim 1 wherein said aging after completion of the continuous feeding of said alkylmercaptan is carried out at a temperature ranging from 25° C. to 50° C. over not less than 6 hours.

3. A process as claimed in claim 1 wherein distillation with boiling after completion of the aging is carried out at a temperature of 100~120° C. while at least one gas selected from the group of air, steam and nitrogen gas is flushed into said reaction vessel.

4. A process as claimed in claim 1 wherein said anion exchanger is a weakly basic anion exchange resin which has as ion-exchange group a tertiary amine or polyamine.

5. A process as claimed in claim 1 wherein the reaction mixture is contacted with said anion exchanger and subsequently with an organic material-absorbing resin.

6. A process as claimed in claim 1 wherein said alkylmercaptan is 2-mercaptoethanol and said alkanesufonic acid is 2-hydroxyethylsulfonic acid.

* * * * *

UNITED STATES PATENT AND TRADEMARK OFFICE
CERTIFICATE OF CORRECTION

PATENT NO. : 5,912,385
DATED : June 15, 1999
INVENTOR(S) : K. Kushibe

It is certified that error appears in the above-identified patent and that said Letters Patent is hereby corrected as shown below:

Title page,
Item [56], References Cited, U.S. PATENT DOCUMENTS, insert
-- 4,987,250   1/1991   McGee, et al. --

Item [57], ABSTRACT, line 2, "alkanesulfionic" should read -- alkanesulfonic --

Column 1,
Line 39, "chern." should read -- chem. --

Column 3,
Line 37, "...$O \leqq x8$)" should read -- ...$O \leqq x \leqq 8$) --.

Column 4,
Line 44, "2-mercaptoethianol" should read -- 2-mercaptoethanol --.

Column 5,
Line 30, "isethiionic" should read -- isethionic --

Column 6,
Line 4, "IRA-945" should read -- IRA-94S --
Line 48, "inercaptoethanol" should read -- mercaptoethanol --.

Column 7,
Line 20, "mercaptoelhanol" should read -- mercaptoethanol --.

Signed and Sealed this

Twenty-third Day of April, 2002

Attest:

*Attesting Officer*

JAMES E. ROGAN
*Director of the United States Patent and Trademark Office*